United States Patent [19]

Giaever

[11] 4,092,116
[45] May 30, 1978

[54] METHOD FOR BINDING ANTIBODIES TO A SURFACE SUCH THAT THEY REMAIN ACTIVE

[75] Inventor: Ivar Giaever, Schenectady, N.Y.
[73] Assignee: General Electric Company, Milwaukee, Wis.
[21] Appl. No.: 608,349
[22] Filed: Aug. 27, 1975

Related U.S. Application Data

[63] Continuation-in-part of Ser. No. 392,950, Aug. 30, 1973, abandoned.

[51] Int. Cl.² ............... G01N 33/16; G01N 31/02
[52] U.S. Cl. .................... 23/230 B; 23/253 TP; 195/103.5 R; 195/103.5 A; 195/103.5 V; 424/12
[58] Field of Search ............. 23/230 B, 253 TP; 424/12; 195/103.5 R, 103.5 A

[56] References Cited

U.S. PATENT DOCUMENTS

| 2,770,572 | 11/1956 | Eldon ...................................... 424/11 |
| 3,551,555 | 12/1970 | Schuurs .................................. 424/12 |
| 3,853,467 | 12/1974 | Giaever .............................. 23/230 B |
| 3,960,489 | 6/1976 | Giaever .............................. 23/230 B |

OTHER PUBLICATIONS

Kabot, "Experimental Immunochemistry," 62–63.
W. D. Harkins, J. Biol. Chem., 132, 111–118, (1940).
Kwapinski, Method Immunochem.
A. E. Gurvich, Nature, vol. 203, 648–649, (1964).
Langmuir et al., J.A.C.S., vol. 59, 1406, (1937).
A. Rothen, Physiological Chem. and Physics, vol. 5, 243–258, (1973).
L. Vroman, Federation Proceedings, vol. 30, 1494–1502, (1971).
I. Giaever, J. of Immunology, vol. 110, 1424–1426, (1973).
F. S. Jones, J. of Experimental, Med., vol. 48, 183–192, (1928).
J. B. Bateman, J. of Immuno., vol. 41, 321–341, (1941).
L. A. Chambers, J. of Immuno., vol. 41, 483–496, (1941).
T. Ogata, J. of Immuno., vol. 69, 13–25, (1952).

*Primary Examiner*—Sidney Marantz
*Attorney, Agent, or Firm*—Morgan, Finnegan, Pine, Foley & Lee

[57] ABSTRACT

In carrying out an immunological reaction or diagnostic test, an immunologically inert organic compound of sufficient quantity is added to an aqueous medium containing an immunologically reactive antigen. A substrate is then treated with the aqueous medium and on the surface thereof is formed, by adsorption, a monomolecular layer of the reactive antigen molecules separated from each other to distances of several hundred Angstrom by the inert organic molecules. Subsequent immersion of the coated substrate in aqueous media alternately containing an immunologically reactive antibody specific to the antigen, and then again containing the reactive antigen, forms a multimolecular immunologically complexed film on the substrate.

58 Claims, 4 Drawing Figures

4,092,116

METHOD FOR BINDING ANTIBODIES TO A SURFACE SUCH THAT THEY REMAIN ACTIVE

CROSS-REFERENCE TO RELATED APPLICATION

This application is a continuation-in-part application of application Ser. No. 392,950 entitled "Method for Binding Antibodies to a Surface Such That They Remain Active" filed Aug. 30, 1973, now abandoned.

FIELD OF THE INVENTION

This invention relates to a method for forming a multimolecular immunologically complexed film on a substrate, and in particular, to a method for binding antibodies to antigens to which they are specific such that some active sites of the antibodies remain active for subsequent immunological reaction.

BACKGROUND OF THE INVENTION

This application contains subject matter which is related to that in concurrently filed application Ser. No. 392,951 entitled "Method For Improving Contrast in Surface Immunological Tests With Large Size Proteins" filed Aug. 30, 1973, now abandoned and patent applications Ser. No. 266,278 entitled "Method and Apparatus for Detection and Purification of Proteins and Antibodies" filed June 26, 1972 now abandoned and Ser. No. 384,113 entitled "Improved Method and Apparatus for Detection and Purification of Proteins and Antibodies" filed July 30, 1973, now abandoned all having a common applicant and assignee.

Other publications which relate to the present invention primarily as background are "Optical Measurement of the Thickness of a Film Adsorbed from a Solution", authors Irving Langmuir et al, Journal of the American Chemical Society, Vo. 59 (July – December 1937) page 1406; "Immunologic and Enzymatic Reactions Carried Out at a Solid-Liquid Interface" by Alexandre Rothen, Physiological Chemistry and Physics, 5, (1973), pages 243–258, "Interactions Among Human Blood Proteins at Interfaces", Leo Vroman et al, Federation Proceedings, Vo. 30, No. 5 (Sept. – Oct. 1971) pages 1494–1502, and "The Antibody-Antigen Reaction: A Visual Observation", Ivar Giaever, The Journal of Immunology, Vol. 110, No. 4 (May 1973) pages 1424–1426.

Immunological reactions are highly specific interactions in which an antigen interacts with a second biological constituent specific to the antigen and generally known as the antibody to form an immunological complex. Immunological reactions taking place within a biological system such as an animal or a human being are vital in combating disease. In a biological system, the entry of a foreign protein, i.e., the antigen, causes the biological system to produce the specific antibody proteins to the antigen in a process not fully understood at this time. The antibody protein molecules have available chemical combining or binding sites which complement those on the antigen molecule so that the antigen and antibody combine or bond to form the immunological complex.

Most antigens are proteins or contain proteins as an essential part, whereas all antibodies are proteins. Proteins are large molecules of high molecular weight, specifically, they are polymers consisting of chains of amino acids. The antigen and antibody protein may each have several combining sites. The five major classes of antibodies (immunoglobulins IgG, IgM, IgA, IgE, and IgD) are each apparently characterized by at least two heavy (long) peptide chains of amino acids and at least two light (short) peptide chains of the acids wherein the bond between the amino acid units is known as a peptide bond. These heavy and light peptide chains are oriented in the general shape of the letter "Y" and the active or combining sites are the extreme ends of the two arms of the Y-shaped antibody for the IgG antibody.

In addition to the immunological reaction which occurs between specific protein antigens and specific protein antibodies resulting in the formation of a protein antigen-protein antibody complex, other immunological complexing reactions between immunologically reactive antigens and antibodies are also contemplated by this invention. In addition, specific reactions between other biological particles, such as enzymes and substrates are also among the test methods contemplated and are embraced by the term "immunological reaction" as used herein. As used herein the terms "antigen" and "antibody" include enzymes and substrates and similar biological particles.

For instance, the following systems include biological particles which are capable of undergoing the immunological reactions described herein:
Viruses
Bacteria and Bacterial toxins
Fungi
Parasites
Animal tissue
Animal body fluids, and the like.

With respect to viruses, the antigens are viral cultures or parts thereof and the antibody specific thereto can be produced by administration of the antigens to a living host. Illustratively, antigen-antibody complexes in the following virus systems are useful in the herein disclosed procedure: Rubella virus culture (antigen) — Rubella virus antibody; polio virus culture (antigen) — polio virus antibody; vesicular stomatitis virus (VSV) culture (antigen) — VSV antibody.

Regarding bacteria and bacterial toxins, the antigens are the particular bacteria or bacterial toxin or parts thereof and the antibody is produced by injection of the antigen into a living host. The following are illustrative examples of antigen-antibody pairs which can be used in the present method: tetanus toxoid suspension (antigen) — tetanus antibody; diphtheria toxin suspension (antigen) — diphtheria antibody; Neisseria gonorrhoeal suspension (antigen) — gonorrhea antibody; Treponema pallidum suspension (antigen) — syphilis antibody.

As for fungi, the antigens are antigenic extracts of fungal suspensions and the antibody is the fungal antibody produced by injection into a living host. Antigen-antibody complexes of fungi systems are illustrated by the following: Aspergillus extract suspension (antigen) — aspergillus fungus antibody; Candida extract suspension (antigen) — candida fungus antibody.

Antigens and antibodies in parasite systems are tested in a similar fashion to those of fungi. The system Toxoplasma gondii extract (antigen) — Toxoplasma gondii antibody is a typical example.

By the term polysaccharides is meant a system wherein the antigen is a carbohydrate antigen. An example of such an antigen-antibody containing system is pneumococcus polysaccharides (antigen) — pneumococcus antibody.

In addition to the typical enzyme - enzyme substrate reaction which is intended to be covered herein, enzymes themselves or parts thereof may be utilized an antigens and the antibody is the particular enzyme antibody elaborated by a living host after injection. Illustrative antigen-antibody complexes of enzyme systems are:

Trypsin extract - trypsin antibody
chymotrypsin extract - chymotrypsin antibody
pepsin extract - pepsin antibody
ribonuclease extract - ribonuclease antibody
thrombin extract - thrombin antibody
amylase extract - amylase antibody
penicillinase extract - penicillinase antibody With respect to hormones, the antigenic constituent is usually found in a hormone extract and the antibody is the particular hormone antibody elaborated by the living organism after injection. An exemplary antigen-antibody complex is:

insulin - insulin antibody

Although the ensuing discussion is directed for the most part to immunological interactions between specific protein antigens and specific protein antibodies, it is understood that it also applies to the systems and the immunologically reactive antigens and antibodies hereinabove described.

Immunological reactions can be detected by various techniques including the use of a suitable substrate such as a metallized glass or metal slide. Exposure of the substrate to an aqueous medium containing antigen will result in the antigen being physically adsorbed in a dense monomolecular layer onto the surface of the substrate. Subsequent exposure of the antigen-coated substrate to a serum containing antibodies specific to the antigen results in the immunological reaction wherein the antibodies selectively attach themselves to the antigens by means of the binding sites on the antibody molecule which complement those on the antigen molecule to thereby form at least a partial bimolecular layer of immunologically complexed antigen-antibody on the substrate surface. The problem arises in a subsequent exposure of the coated substrate containing the antigen-antibody complex to an aqueous medium containing, or suspected of containing, the same antigen. This subsequent exposure will generally result in no further binding of antigen to antibody since all of the active sites of the antibodies are already bound to the first antigenic layer due to the active antigenic molecules being very closely spaced together. Thus, there is a problem in surface immunology of the antibodies binding to a (antigen) surface and losing their activity (i.e., ability to further bind with an antigen, cell or virus).

Therefore, one of the principal objects of this invention is to provide a new method for binding antibodies to a surface so that the antibodies remain active.

A further object of this invention is to provide a new method for binding antibodies to an adsorbed antigen layer with combining sites of the antibodies remaining active for a further immunological reaction.

Another object of this invention is to provide a new method for forming multimolecular immunologically complexed films.

SUMMARY OF THE INVENTION

In accordance with this invention, an immunologically inert organic compound is added to an aqueous medium containing an immunologically reactive antigen. A substrate is then treated with the aqueous medium and the surface of the substrate is coated, by adsorption, with a monomolecular layer of the antigen molecules and inert organic compound molecules. The quantity of inert organic compound molecules is sufficient so that the adsorption layer consists of reactive antigen molecules separated from each other to average distances of several hundred Angstroms by the inert organic molecules. Subsequent immersion of the coated substrate in an aqueous medium containing an immunologically reactive antibody specific to the antigen results in the antibody molecules bonding with the antigen molecules, but leaving the remaining antibody sites active. As a result, subsequent immersion of the coated substrate to an aqueous medium suspected of containing the antigen results in further attachment thereof to the active sites of the antibodies that are bound to the first antigenic layer. Thus, this invention can be utilized in the analysis of an aqueous medium for detecting the presence of a particular antigen. A subsequent immersion of the coated substrate in aqueous medium alternately containing the same antibody and antigen can build up relatively long chains of antigen-antibody complexes from the surface of the substrate. The method can be used to identify cells or viruses immunologically since the probability for several of the antibody molecules on the ends of the chains of antigen-antibody complexes finding an antigenic site on particular cells or viruses is relatively high irrespective of the irregularity of the surface of the cell or virus.

The features of the invention which are desired to be protected are pointed out with particularity in the appended claims. The invention itself, however, both as to its organization and method of operation together with further objects and advantages thereof, may best be understood by reference to the following description taken in connection with the accompanying drawing wherein like parts in each of the several figures are identified by the same reference character, and wherein:

DETAILED DESCRIPTION OF THE INVENTION

Figure 1:
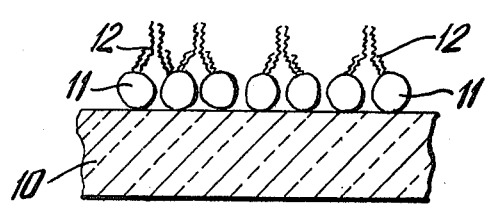
FIG. 1 is an elevation view of a substrate after it has been treated first with an aqueous medium containing an antigen by a known method and then immersed in an aqueous medium containing the antibody specific to the antigen.

Referring now to FIG. 1, there is shown a highly magnified elevation view of a portion of diagnostic apparatus in the form of a thin wafer 10 of suitable substrate material which may be metal, glass, mica, plastic, fused silica, quartz or similar material, with metal being preferred as having the greatest difference in refractive index to protein and preferably is in the form of a metal or metallized glass slide. A detailed discussion of substrate metallization is found in the aforementioned copending patent applications Ser. No.

384,113 entitled "Method and Apparatus for Detection and Purification of Proteins and Antibodies" filing date July 30, 1973 and Ser. No. 266,278 entitled "Method and Apparatus for Detection and Purification of Proteins and Antibodies" filing date June 26, 1972, both having a common assignee. Substrate 10 when treated with a first aqueous medium, which may be biologically an antigen or antibody dissolved in salt water, has it adsorbed onto the substrate in a monomolecular layer 11. For the purpose of this invention, the treatment may be by applying a drop of aqueous medium or by partial or complete immersion in the aqueous medium, but for simplification, the layer 11 adsorbed on the surface of substrate 10 will hereinafter be described as antigen layer. Any antigen or antibody will adsorb in such monomolecular layer, but no further adsorption will take place, that is, the antigen or antibody will attach to the substrate, but will not attach to itself. Thus, the antigen layer 11 can only be monomolecular and not of greater thickness. The time required to completely coat the substrate with the antigen is a function of the concentration of the antigen in the aqueous medium, the degree of agitation of the aqueous medium and the medium temperature. As as example, a 1% bovine serum albumin solution completely coats a slide in approximately 30 minutes with a monomolecular antigen layer.

After the monomolecular layer of antigen 11 has formed over substantially the entire surface of the substrate 10, the coated substrate is removed from the aqueous medium containing the antigen, and is next immersed in an aqueous medium containing, or suspected of containing, the specifically reacting antibody to the antigen. This second aqueous medium may contain many constituents in addition to the specifically reacting antibody whose presence it is desired to detect. However, no antibody other than the specifically reacting antibody will adhere to the first antigen layer on the substrate. Thus, only if the specifically reacting antibody is present in the second aqueous medium will immunological complexing between the antigen and its specifically reacting antibody take place and the substrate will, after a time, have a bimolecular layer thereon. The time required for the adhesion of the second (antibody) molecular layer 12 onto the coated substrate is again a function of the concentration of the specifically reacting protein in the aqueous medium, the degree of medium agitation, and medium temperature. For antibodies in blood serum, this timing may be as long as one day, or as short as minutes depending on the concentration. The second layer may be only a partial one, or substantially complete, depending upon the above three enumerated factors.

As illustrated in FIG. 1, in the case wherein the antigen layer 11 substantially completely coats substrate 10, i.e., the spacing between adjacent antigen molecules is minimal, the antibody molecules utilize substantially all of their combining sites to bind to the antigen molecules so as to lose their activity, that is, substantially all of the active sites on the antibody molecules 12 combine with corresponding active sites on the antigen molecules 11. This substrate coating process is described in copending patent application Ser. No. 266,278 entitled "Method and Apparatus for Detection and Purification of Proteins and Antibodies", filing date June 26, 1972, and having a common applicant and assignee.

Figure 2:
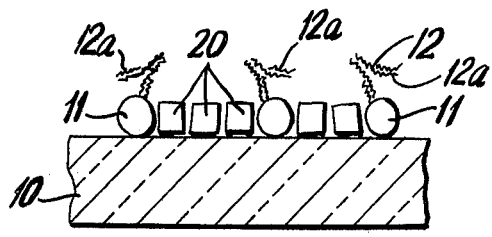
FIG. 2 is an elevation view of the substrate after it has undergone two steps as in FIG. 1, but with the first treatment being in accordance with the invention.

Due to the monomolecular antigen layer 11 being adsorbed over substantially the entire surface of substrate 10 in FIG. 1, the second layer 12 of the specific antibody for such antigen bonds thereto to form the bimolecular layer and no further combining with additional antigen is possible since there are no remaining active sites on the antibody molecules in layer 12. In the present invention, a method is disclosed by which the antibody molecules in the second layer 12 can be bound with the antigen molecules in the first layer 11 while at the same time having sites remaining active for further combining with other antigen molecules in a further immunological reaction. The basis of this present discovery is illustrated in FIG. 2 and is involved in the method of forming the initial monomolecular layer of antigen molecules 11 which are adsorbed onto the surface of substrate 10. For purposes of illustration, the antibodies depicted herein are of the IgG class, but there are no reasons why antibodies of the other four major classes enumerated above cannot be utilized in this invention.

After selection of the substrate 10 on which the multimolecular immunologically complexed film is to be formed, such substrate is treated with a first aqueous medium, e.g. a salt water solution containing the antigen as in the case of the method described hereinabove with reference to FIG. 1. But in contradistinction with such previous method, an immunologically inert organic compound has been added to the first aqueous medium prior to treatment with the substrate therein such that the adsorption layer formed on the surface of substrate 10 consists of the reactive antigen molecules 11 separated from each other and surrounded along the substrate surface by inert organic compound molecules 20 as seen in FIG. 2. The quantity of the immunologically inert organic compound added to the aqueous medium is sufficient such that the average spacing between adjacent antigen molecules 11 adhering to substrate 10 will generally be to distances of several hundred Angstroms.

The inert organic compound can vary as to chemical type, it being only required that the protein not stick to it. Merely by way of illustration, one can use egg albumen, bovine serum albumen, insulin and the like. The concentrations employed will in general range from 0.05 to 100 mg./ml. of the aqueous medium, with the amount selected to depend on the concentration of antigen.

The antigen-inert constituent monomolecular coated substrate 10 is then immersed in a second aqueous medium containing the antibodies specific to the antigen in the first medium. Since the spacing between the active sites of an antibody molecule 12 (of the IgG Class) is approximately 200 Angstrom, a large fraction of the antibody molecules 12 in the second medium which combine with the antigen molecules 11 will have their remaining combining sites (and there may be more than one remaining active site per molecule, depending upon the particular class of antibody molecule) remain active for further combination with additional antigen molecules in a subsequent immunological reaction. Any one antibody molecule cannot in general combine with more than one active site on any one antigen molecule. Thus, as seen in FIG. 2, due to the sufficient spacing between adjacent antigen molecules 11 by means of the immunologically inert organic compound molecules 20, the antibody molecules 12 are bound to the antigen molecules 11 and in general each antibody molecule 12 has a combining site 12a remaining active for a subsequent immunological reaction. One of the principal objects of the invention has thus been achieved, antibodies have been bound to a monomolecular antigen layer surface such that combining sites of the antibodies remain active for further immunological reactions. In the case of the active antigen being human serum albumen, the immunologically inert protein is egg albumen, as one example, and the antibodies are obtained from a rabbit serum. In the case of a 1% human serum albumen solution, the concentration of the inert egg albumen protein therein is in the range of 1-10%.

Figure 3:
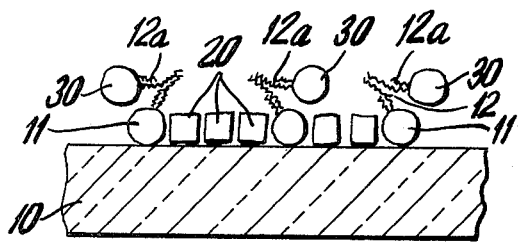
FIG. 3 is an elevation view of the substrate of FIG. 2 after a subsequent immunological reaction wherein the coated substrate is immersed in an aqueous medium containing the same antigen.

Referring now to FIG. 3, after the substrate 10 has been removed from the antibody containing aqueous medium (i.e., after the steps shown in FIG. 2), the bimolecular coated substrate 10 is next immersed in an aqueous medium containing, or suspected of containing, the same antigen as in the first aqueous medium, and such antigen molecules 30 will selectively bind to the remaining active sites 12a of the antibody molecules 12 in a further immunological reaction. This procedure can thus be utilized in the analysis of a solution for readily detecting the presence of a particular antigen therein. Alternatively, this procedure can be used to cause a buildup of several chains of alternating antigen-antibody molecules wherein each chain has its origin at the surface of substrate 10 to thereby form a multimolecular immunologically complexed film of the several chains of alternating antigen-antibody molecules thereon. The multimolecular complexed film is readily verified by viewing the coated substrate with an optical instrument such as an ellipsometer. Alternatively, and as described in greater detail in the aforementioned copending patent application Ser. No. 266,278, as well as copending application Ser. No. 384,113, filed July 30, 1973, the multimolecular complexed film can also be examined electrically by measuring the electric capacitance of a capacitor having conducting plates formed by the metal or metal coated substrate and a mercury drop or other suitable electrode, and the capacitor dielectric being the constituent layers. Also, as described in the aforesaid copending applications, the multimolecular complexed film can be examined optically by unaided visual observation by determining the length of time before a visible amalgam is formed between a drop of mercury and metal film coated on the substrate with the layers therefrom. Finally, and most importantly, the multimolecular complexed film can be examined optically by reflected light or transmitted light as explained in the aforesaid copending applications. In this latter optical examination by reflected or transmitted light, the following is a first transmitted light technique which has successfully been used: The substrate 10 which must be a light transmissive substrate such as glass, plastic, fused silica, mica, quartz, or the like, and is preferably glass, with microscope slides being a conveniently available source, is first coated with a plurality of metal globules by evaporating a metal, for example, indium, onto the substrate. For example, the indium is evaporated slowly from a tantalum boat onto the glass substrate in an ordinary vacuum of about $5 \times 10^{-5}$ mm of mercury. Because the indium atoms have high mobility on the surface of the substrate and do not wet the glass substrate significantly, the indium evaporated onto the substrate agglomerates into small particles. Any metal having similar characteristics so that it will form globules on the substrate when evaporated thereon may be used. In addition to indium, gold, silver, tin bismuth, and lead have been successfully used. The evaporation of metal is continued until the substrate appears light brown in color. At this point, the metal globules have diameters on the order of 1000 A. The precise size of the globules is not critical but they must have diameters equal to a large fraction of the wavelengths of visible light. The next step is to treat the globule-covered substrate 10 with an aqueous medium containing a first immunologically reactive antigen 11 and the inert organic compound 20. The first reactive antigen and inert organic compound again adhere in a monomolecular layer over the substrate and the metal globules thereon. When a monomolecular layer has formed, the coated substrate is then removed from the first aqueous medium and immersed in a second aqueous medium containing the specifically reacting antibody 12 to the first antigen and results in the substrate and metal globules having a bimolecular layer adhering thereto similar to that shown in FIG. 2 (i.e., without the metal globules). The coated substrate is then removed from the second aqueous medium and immersed in a third aqueous medium which contains, or is suspected of containing the reactive antigen in the first aqueous medium; if the antigen is present, then a third layer (or partial layer) is formed on the substrate. The coated substrate is then viewed by transmitted light, and a determination is made from the appearance of the coated substrate as to the thickness of the layer adhering thereto and accordingly as to the presence or absence of the suspected antigen. The detection of layers corresponds to variations in the shade of brown which is observed in the coated substrate. These variations are quite pronounced and the detection of layers is therefore a simple straightforward procedure. The particles alone on the substrate appear as a first shade of brown, the particles coated with a monomolecular layer appear as a darker shade of brown, the particles covered with a bimolecular layer appear as a still darker shade of brown, and the particles covered with a trimolecular layer appear darker still. This detection method is based on the fact that electromagnetic radiation is scattered to a large degree by conducting spheres having diameters equal to a large fraction of a wavelength of the incident light and that in the case of scattering from such spheres, the scattering is strongly influenced by a thin dielectric coating applied to the spheres.

A second technique for optical examination by reflected light which has successfully been used is as follows: A gold substrate, which, for reasons of economy, is preferably a thin gold layer plated onto another metal, has adsorbed thereon a monomolecular layer of the first reactive antigen 11 and inert organic compound 20 after treatment with the hereinabove identified first aqueous medium. Gold has an adsorption band within the visible spectrum, and this fact accounts for the characteristic color of gold and provides for the operation of this particular optical examination technique. The gold substrate may conveniently be a glass slide coated with a thin indium layer and overcoated with the gold layer wherein indium layer improves both the adhesion between the glass and the gold as well as the optical characteristics of the slide. The relative reflectivity of the gold substrate as a function of wavelength results in the substrate having the characteristic bright yellow color of gold metal in the absence of any protein layer adhering thereon. In the presence of a monomolecular layer on the substrate, the appearance of the test slide (substrate) has a dull yellow appearance. After the test slide has been exposed to an aqueous medium containing the immunological reacting antibody 12 to the antigen 11 which is in the first layer along with the inert organic compound 20, the test slide has a bimolecular layer thereon and a reflectivity characteristic which provides a greenish appearance. A third layer provides an even more greenish appearance. In tests which have been performed to date, it appears that the optical examinations of the coated substrate by reflected or transmitted light and which employ a substrate including metal globules or a gold substrate are the most generally useful. Furthermore, it has been determined that these two techniques have different sensitivities as functions of the thicknesses of protein films of interest. Specifically, the greatest sensitivity of the technique having a substrate including metal globules occurs with films having thicknesses below approximately 200 A. The gold substrate technique has the greatest sensitivity for films exceeding 30 A in thickness. The particular detection method employed thus determines the type of substrate 10 utilized in each analysis, that is, whether the substrate is a metal or metallized glass slide, with a flat metal (gold, as one example) coating or metal (indium, as one example) globules on the surface, as again explained in the above-described copending applications. For purposes of simplification, the substrate 10 is illustrated herein as having a flat surface, although it is to be understood that the surface to which the first antigen layer adsorbs could also contain the aforementioned metal globules.

The herein disclosed method of forming multimolecular (3 layer) immunologically complexed films, as depicted in FIG. 3, is especially important in testing an aqueous medium for a certain biological constituent, for example a hormone, since hormones and antiserum to hormones are generally available. Thus, when the third layer is the hormone of interest, it is easily detectable.

Figure 4:
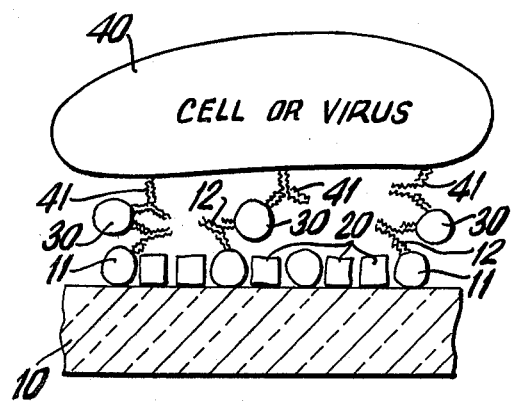
FIG. 4 is an elevation view of the substrate of FIG. 3 after a further immersion of the substrate in an aqueous medium containing the same antibody and wherein the antibody molecules on the ends of the chains of the antigen-antibody complexes find antigenic sites on a virus or cell for identification thereof immunologically.

The forming of multimolecular immunologically complexed films in accordance with this invention is also important in identifying cells or viruses immunologically. Thus, as illustrated in FIG. 4, by building up a plurality of chains of antigen-antibody complexes from the surfaces of substrate 10, the probability for several of the antibody molecules on the end of the various chains to find an antigenic site on a cell or virus 40 is relatively high. And this probability remains high irrespective of the irregularity of the surface of the cell or virus. As is well known, the cell membrane which encloses each cell has molecules extending outward therefrom which are called the "transplantation" antigens. These antigens are the ones utilized in forming the first layer 11 in a two-layer system for identifying cells immunologically wheren the cell of interest would constitute the third layer. In the case of a four-layer system of antigen-antibody chains as depicted in FIG. 4, the first and third layers (11 and 30, respectively) would consist of the transplantation antigens. In like manner, it is well known that a virus has a protein coat of protein molecules which can be split up and separated, and such molecules respectively form the first, and first and third layers in two and four-layer systems of the antigen-antibody chains utilized for identifying a virus 40 immunologically. The antibodies 12 in the second layer and 41 in the fourth layer would, of course, be specific to the particular cell or virus being investigated.

It should be mentioned that the configuration of the substrate used herein is not critical to the invention. Preferably, it is slide shaped, e.g., in the form of metallized glass slides because of the ready availability of such slides. However, it can be in the form of a belt as described in copending application Ser. No. 266,278 referred to above. The only limitation imposed on the substrate is its ability to allow the formation of a monomolecular layer thereon. The dimensions of form will be dictated by the manner in which the test is carried out including subsequent analysis and its objective. If it is for collection of a particular immunologically active biological constituent a belt is preferred for reasons discussed in copending application Ser. No. 266,278.

The term "immunologically inert organic compound" embodies any organic substrate, e.g., proteinaceous or nonproteinaceous material which is non-reactive to the interacting constituents and has no effect on the complexing molecules. It must, however, have the ability to adhere to the substrate, and to separate and surround the antigen molecules.

The contrast provided by multilayer adsorption can be enhanced to an even greater extent by depositing the antigen and inert organic compound on substrate 10 as a single drop of the aqueous medium, and subsequently immersing the drop-coated substrate into an aqueous medium containing only the inert organic compound 20 so as to form a monomolecular layer of the small antigen-inert organic compound area completely surrounded by the inert compound. This feature results in overcoming the problem of non-specific adsorption in the case where the antibodies are in a serum since the inert compound along the remaining surface of the substrate prevents non-specific sticking by constituents in the serum to the substrate and thereby improves the contrast.

DESCRIPTION OF THE PREFERRED EMBODIMENTS

The following examples, which are to be regarded as illustrative and not limiting, show how surface immunological tests are carried out according to this invention.

EXAMPLE 1

A diagnostic test for hepatitis antigen is carried out as follows: A glass slide is metallized with a layer of indium metal globules. A solution of 1 mg./ml. of hepatitis-associated antigen in 0.85% saline is prepared, and to this is added bovine serum albumin to provide a concentration of 0.1 mg/ml. (BSA). A drop of the solution of antigen and inert protein is placed in the center of the slide. The slide is incubated in a moist chamber (plastic box filled with wet sponges) at 23° C. until the antigen adheres to the metallized surface (10–30 minutes). The slide is washed with distilled water and blown dry with a jet of air. The inert protein covers about ¾ of the circular area of the dry adsorption layer, and the antigen about ¼, leaving a major portion of the latter molecules exposed. The slide is then exposed to a preparation of anti rabbit HAA serum which contains antibody to hepatitis-associated antigen. This produces a bimolecular layer in which a large fraction of the outwardly exposed antibody molecules have remaining combining sites. The slide and antibody solution are incubated at 20° C. for 10 minutes. After incubation, the slide is again washed with distilled water. The test slide is exposed to a solution suspected of containing the hepatitis-associated antigen as described above. The formation of a sharply contrasting visible spot on the slide indicates a positive reaction. In cases where the suspected solution does not contain antibodies to hepatitis-associated antigen, no trimolecular layer will form.

EXAMPLES 2 – 6

Diagnostic tests according to this invention are carried out by the procedure of Example 1 substituting the following substrates, antigens, immunologically inert organic compounds, and antibody preparations:

| Ex. | Substrate | Antigen | Inert Organic Compound | Antibody Source |
|---|---|---|---|---|
| 2 | Indium metallized glass | hepatitis-associated | egg albumin | rabbit blood serum |
| 3 | indium metallized glass | hepatitis-associated | insulin | rabbit blood serum |
| 4 | gold metallized glass | hepatitis-associated | bovine serum albumin | rabbit blood serum |
| 5 | tantalum metallized glass | hepatitis-associated | bovine serum albumin | rabbit blood serum |
| 6 | indium metallized glass | insulin | bovine serum albumin | rabbit blood serum |

From the foregoing description, it can be appreciated that this invention makes available a new method for binding antibodies to a surface such that they remain active and for forming multimolecular immunologically complexed films on a substrate by the addition of an immunologically inert organic compound of sufficient quantity to a first aqueous medium containing an immunologically reactive antigen. Treatment of a suitable substrate in the first aqueous medium forms, by adsorption, on the surface thereof a monomolecular layer of the reactive antigen molecules separated from each other by the inert organic compound molecules. The formation of such particular monomolecular layer then permits subsequent immersion of the coated substrate in a second aqueous medium which contains the antibody specific to the first antigen, so that the antibody molecules bond to the antigen molecules while having other active sites free to interact in subsequent immunological reactions. The coated substrate can be subsequently immersed in an aqueous medium containing, or suspected of containing, the same antigen as in the first solution, and such procedure can be repeated to cause a build up of several chains of alternating antigen-antibody molecules.

Having described the invention with reference to particular embodiments and examples, it is believed obvious that modification and variation of this invention is possible in the light of the above teachings. Thus, the inert organic compound could be in an aqueous medium separate from the antigen, and the substrate would be treated therewith as a preliminary step, or as an intermediate step between treatments with a dilute aqueous medium containing the antigen and the antibody. As another approach, in the case where the antibodies are in a serum, a dilute solution of the antigen would be utilized in forming an incomplete first layer on the substrate, and the inert organic compound would be omitted in such solution since the non-specific proteins in the serum would function as the inert constituent in adhering to the substrate and thereby act as the spacing agents between the antigen molecules. This invention can also be used for detecting enzymes by utilizing a dilute solution of the enzyme for obtaining the antigens in the first layer, and adding bovine serum albumin as the inert constituent to the first solution, utilizing a solution of an antibody to the enzyme (from a rabbit previously injected with the enzyme) in the second solution, and then immersing the bimolecular coated substrate in a third solution suspected of containing the enzyme, and then examining the substrate for the presence of a third layer which would be the particular enzyme. Finally, although the reactive protein adsorbed on the substrate surface has been described hereinabove as being an antigen, it should be evident that such first layer reactive protein could be an antibody, and the second layer protein would then be the antigen specific to such antibody, and the third layer would again be the antibody. It is, therefore, to be understood that changes may be made in a particular embodiment of this invention as described which is within the full intended scope of the invention as defined by the following claims.

I claim:

1. A method for binding reactive constituents to a surface so that they remain active comprising the steps of coating a metallized slide with a monomolecular layer of a reactive first constituent and inert organic compound so that the first constituent molecules are separated from each other by inert organic molecules, and subsequently exposing the coated slide to an aqueous medium containing a reactive second constituent specific to the first constituent to cause a reaction therewith in which the second constituent molecules bond with the first constituent molecules to form a bimolecular layer on the slide, the inert organic compound being of sufficient quantity to obtain sufficient average spacing between adjacent first constituent molecules in the monomolecular layer so that the second constituent molecules retain active sites for a further immunological reaction.

2. A method as defined in claim 1 wherein said reaction is between a protein antigen and a protein antibody specific to the antigen, said inert organic compound is an inert protein and said aqueous media are solutions.

3. The method set forth in claim 1 wherein the reactive first constituent is an antigen, and the reactive second constituent is an antibody specific to the antigen.

4. The method set forth in claim 1 wherein the reactive first constituent is an antibody, and the reactive second constituent is an antigen to which the antibody is specific.

5. A method as defined in claim 1 wherein the step of coating the slide with a monomolecular layer of a first constituent and inert organic compound comprises forming a first aqueous medium of the reactive first constituent, adding the inert organic compound of sufficient quantity to the first aqueous medium, contacting the slide with the first aqueous medium to coat all or part of the slide with the monomolecular layer of the first constituent and the inert organic compound, and removing the monomolecular layer coated slide from the first aqueous medium.

6. A method as defined in claim 5 wherein said immunological reaction is between a protein antigen and a protein antibody specific to the antigen, said inert organic compound is an inert protein and said aqueous media are solutions.

7. A method as defined in claim 1 wherein the metallized slide also includes a metal oxide layer intermediate the metal of the slide and said monomolecular surface.

8. A method as defined in claim 7 wherein said metal is titanium and said oxide is an oxide of titanium.

9. A method as defined in claim 1 wherein said metallized slide is a metal slide or a metallized glass slide.

10. A method as defined in claim 9 wherein the metal comprising the slide is selected from indium, gold, silver, tin and lead.

11. A method as defined in claim 9 wherein said metallized slide comprises indium on a glass slide.

12. A method as defined in claim 9 wherein said metallized slide comprises gold on a glass slide.

13. A method as defined in claim 9 wherein said metallized slide comprises a glass slide coated with a thin indium layer and overcoated with a gold layer.

14. A method for binding antibodies to a surface so that they remain active comprising the steps of forming an aqueous medium containing an immunologically reactive antibody, adding a sufficient quantity of an immunologically inert organic compound to said medium, and exposing a metallized slide to the aqueous medium to coat at least a portion of the slide by absorption with a monomolecular layer of the antibody and the inert organic compound wherein the antibody molecules are sufficiently spaced from each other by the sufficient quantity of inert organic molecules so that the antibody molecules present a greater number of active sites which are retained for a further immunological reaction than if the antibody molecules were closely spaced together.

15. A method as defined in claim 14 wherein said immunological reaction is between a protein antigen and a protein antibody specific to the antigen, the inert organic compound is an inert protein and said media are aqueous solutions.

16. The method of claim 14 wherein said substrate is a metallized glass slide.

17. The method of claim 16 wherein the metal comprising the slide is selected from indium, gold, silver, tin and lead.

18. The method of claim 17 wherein the substrate comprises indium on a glass slide.

19. The method of claim 17 wherein the substrate comprises gold on a glass slide.

20. The method of claim 17 wherein the substrate comprises a glass slide coated with a thin indium layer and overcoated with a gold layer.

21. The method for determining the presence or absence of a suspected constituent in an aqueous medium comprising the steps of forming a first aqueous medium containing an immunologically reactive antigen, adding a quantity of inert organic compound to the first aqueous medium, contacting a metal slide or a metallized glass slide with said aqueous medium to coat all or part of the slide with a monomolecular layer of the antigen and the inert organic compound, the quantity of inert compound being sufficient to provide that the antigen molecules are separated from each other by the inert organic molecules, removing the monomolecular layer coated substrate from the first aqueous medium, subsequently exposing the coated substrate to a second aqueous medium containing an immunologically reactive antibody specific to the antigen to cause an immunological reaction therewith in which the antibody molecules bond with the antigen molecules to form a bimolecular layer on the substrate, and the antibody molecules retain a significantly greater number of active sites for a further immunological reaction than if the antigen molecules were closely spaced together, removing the bimolecular layer coated substrate from the antibody containing medium, exposing the coated substrate to a third aqueous medium suspected of containing the same antigen which is in the first aqueous medium and causing an immunological reaction to occur with the antibody in which the remaining active sites on the antibody molecules bond with the antigen molecules in the third aqueous medium, and examining the coated substrate to determine whether there is a third layer thereon thereby indicating the presence of the antigen in the third aqueous medium.

22. A method as defined in claim 21 wherein said immunological reaction is between a protein antigen and a protein antibody specific to the antigen, said inert organic compound is an inert protein and said aqueous media are solutions.

23. The method of claim 21 wherein said metallized slide also includes a metal oxide layer intermediate the metal of the slide and said monomolecular surface.

24. A method as defined in claim 23 wherein said metal is titanium and said oxide is an oxide of titanium.

25. The method of claim 21 wherein said examining step comprises visually viewing the coated substrate by transmitted light.

26. The method of claim 25 wherein said metal is indium and the visual determination is made by distinguishing among four shades of brown.

27. The method of claim 21 wherein the metal comprising the substrate is selected from indium, gold, silver, tin and lead.

28. The method of claim 27 wherein the substrate comprises indium on a glass slide.

29. The method of claim 27 wherein the substrate comprises gold on a glass slide.

30. The method of claim 27 wherein the substrate comprises a glass slide coated with a thin indium layer and overcoated with a gold layer.

31. A method for forming multimolecular immunologically complexed films comprising the steps of treating a metallized substrate with a monomolecular layer of an immunologically reactive antigen and an immunologically inert organic compound so that the antigen molecules are separated from each other by the inert organic compound molecules, and subsequently exposing the treated substrate to an aqueous medium containing an immunologically reactive antibody specific to the antigen to cause an immunological reaction therewith in which the antibody molecules bond with the antigen molecules to form a bimolecular layer on the substrate, and the antibody molecules retain a significantly greater number of active sites for a further immunological reaction than if the antigen molecules were closely spaced together.

32. A method as defined in claim 31 wherein said metallized substrate is slide shaped, said immunological reaction is between a protein antigen and protein antibody specific to the antigen, said inert organic compound is an inert protein and said aqueous medium is a solution.

33. A method as defined in claim 31 wherein said antigen is derived from a bacteria, a virus, a fungus, mammalian tissue or mammalian body fluids.

34. A method as defined in claim 31 wherein said inert organic compound is selected from bovine serum albumin, egg albumin or insulin.

35. A method as defined in claim 31 wherein the step of treating the substrate with a monomolecular layer of an antigen and inert organic compound comprises the steps of forming a first aqueous medium containing the immunologically inert organic compound, immersing the substrate in the first aqueous medium containing the immunologically inert organic compound, immersing the substrate in the first aqueous medium sufficiently to coat the substrate with a partial monomolecular layer of the inert organic compound, removing the partially coated substrate from the first aqueous medium, forming a second aqueous medium containing the immunologically reactive antigen, immersing the partially coated substrate in the second aqueous medium to coat the remaining surface of the substrate with a partial monomolecular layer of the antigen so that the monomolecular layer consists of an antigen molecules separated from each other by the inert organic molecules, and removing the monomolecular layer coated substrate from the second aqueous medium.

36. A method as defined in claim 35 wherein said metallized substrate is slide shaped, said immunological reaction is between a protein antigen and a protein antibody specific to the antigen, said inert organic compound is an inert protein and said aqueous media are solutions.

37. A method as defined in claim 31 wherein the step of treating the metallized substrate with a monomolecular layer of an antigen and inert organic compound comprises the steps of forming a dilute first aqueous medium containing the immunologically reactive antigen, immersing the substrate in the first aqueous medium sufficiently to coat the substrate with a partial monomolecular layer of the antigen, removing the partially coated substrate from the first aqueous medium, forming a second aqueous medium containing the immunologically inert organic compound, immersing the partially coated substrate in the second aqueous medium to coat the remaining surface of the substrate with a partial monomolecular layer of the inert organic compound so that the monomolecular layer consists of the antigen molecules separated from each other by the inert organic molecules, and removing the monomolecular layer coated substrate from the second aqueous medium.

38. A method as defined in claim 37 wherein said metallized substrate is slide shaped, said immunological reaction is between a protein antigen and a protein antibody specific to the antigen, said inert organic compound is an inert protein and said aqueous media are solutions.

39. A method as defined in claim 31 wherein the step of treating the metallized substrate with a monomolecular layer of an antigen and inert organic compound comprises the steps of forming a first aqueous medium containing the immunologically reactive antigen, adding the immunologically inert organic compound of sufficient quantity to the first aqueous medium, depositing at least a single drop of the first aqueous medium on the substrate to have the antigen-inert organic compound form a small area monomolecular layer thereon, forming a second aqueous medium containing immunologically inert organic compound, subsequently immersing the drop-coated substrate into the second aqueous medium so as to form a complete monomolecular layer over the entire surface of the substrate which includes the small antigen-inert organic compound area surrounded by the inert organic compound from the second aqueous medium, and removing the monomolecular layer coated substrate from the second aqueous medium.

40. A method as defined in claim 39 wherein said substrate is slide shaped, said immunological reaction is between a protein antigen and a protein antibody specific to the antigen, said inert organic compound is an inert protein and said aqueous media are solutions.

41. A method as defined in claim 31 wherein the antibody is of the immunoglobulin IgG class.

42. A method as defined in claim 41 wherein the antigen in the first aqueous medium is an enzyme, the inert organic compound is bovine serum albumin, and the antibody in the second aqueous medium is obtained from a rabbit previously injected with the enzyme.

43. A method as defined in claim 31 wherein the step of treating the metallized substrate with a monomolecular layer of an antigen and inert organic compound comprises the steps of forming a first aqueous medium containing the immunologically reactive antigen, adding the immunologically inert organic compound of sufficient quantity to the first aqueous medium, contacting the substrate with the first aqueous medium to coat all or part of the substrate with the monomolecular layer of the antigen and inert organic compound, said inert compound being of sufficient quantity so that the antigen molecules are sufficiently separated from each other by the inert organic molecules, and removing the monomolecular layer coated substrate from the first aqueous medium.

44. A method as defined in claim 43 wherein said metallized substrate is slide shaped, said immunological reaction is between a protein antigen and a protein antibody specific to the antigen, said inert organic compound is an inert protein and said aqueous medium is a solution.

45. A method as defined in claim 43 and further comprising the steps of removing the bimolecular layer coated substrate from the antibody containing medium, subsequently exposing the coated substrate to a third aqueous medium suspected of containing the same antigen which is in the first aqueous medium to cause an immunological reaction with the antibody in which the remaining active sites on the antibody molecules bond with the antigen molecules in the third aqueous medium, and examining the coated substrate to determine whether there is a third layer thereon thereby indicating the presence of the antigen in the third aqueous medium.

46. A method as defined in claim 45 wherein said metallized substrate is slide shaped, said immunological reaction is between a protein antigen and a protein antibody specific to the antigen, said inert organic compound is an inert protein and said aqueous media are solutions.

47. The method set forth in claim 43 wherein the step of forming a first aqueous medium containing the immunologically reactive antigen consists of separating the antigens which are in the outermost portions of a particular cell or virus, and forming an aqueous medium thereof prior to adding said inert organic compound thereto, and further comprising the steps of removing the bimolecular layer coated substrate from the antibody containing medium, subsequently immersing the coated substrate in a third aqueous medium suspected of containing the particular cell or virus so that the antibody molecules find antigenic sites on the cell or virus to cause bonding therewith, and examining the coated substrate to determine whether there is a third layer thereon thereby indicating the presence of the particular cell or virus in the third aqueous medium.

48. A method as defined in claim 47 wherein said metallized substrate is slide shaped, said immunological reaction is between a protein antigen and a protein antibody specific to the antigen, the inert organic compound is an inert protein and said aqueous media re solutions.

49. A method as defined in claim 43 wherein the step of adding a sufficient quantity of the immunologically inert organic compound to the first aqueous medium comprises adding a quantity sufficient so that the average spacing between adjacent immunologically reactive antigen molecules absorbed on the surface of the substrate will generally be to distances of several hundred Angstroms.

50. A method as defined in claim 49 wherein said metallized substrate is slide shaped, said immunological reaction is between a protein antigen and an antibody specific to the antigen, said inert organic compound is an inert protein and said aqueous media are solutions.

51. A method as defined in claim 43 and further comprising the steps of removing the bimolecular layer coated substrate from the antibody medium, subsequently exposing the coated substrate to a third aqueous medium containing the same antigen which is in the first aqueous medium to cause an immunological reaction with the antibody in which the remaining active sites on the antibody molecules bond with the antigen molecules in the third aqueous medium.

52. A method as defined in claim 51 wherein said metallized substrate is slide shaped, said immunological reaction is between a protein antigen and a protein antibody specific to the antigen, the inert organic compound is an inert protein and said aqueous media are solutions.

53. The method as defined in claim 51 and further comprising the steps of removing the coated substrate from the third aqueous medium, and subsequently exposing the coated substrate to a fourth aqueous medium containing the same antibody which is in the second aqueous medium to cause an immunological reaction in which first active sites of the antibody molecules in the fourth aqueous medium bond with antigen molecules from the third aqueous medium while having other combining sites remain active to thereby build up chains of antigen-antibody complexes from the surface of the substrate.

54. The method as defined in claim 53 wherein said metallized substrate is slide shaped, said immunological reaction is between a protein antigen and a protein antibody specific to the antigen, the inert organic compound is an inert protein and said aqueous media are solutions.

55. A method as defined in claim 53 and further comprising the steps of removing the coated substrate from the fourth aqueous medium, subsequently exposing the substrate with the chains of antigen-antibody complexes built up from the substrate surface of a fifth aqueous medium suspected of containing cells or virus specific to the antibody in the chains of antigen-antibody complexes, removing the coated substrate from the fifth aqueous medium, and examining the substrate to determine whether active sites remaining on the antibody molecules have combined with antigenic sites on the cells or virus in the fifth aqueous medium.

56. A method as defined in claim 55 wherein said metallized substrate is slide shaped, said immunological reaction is between a protein antigen and a protein antibody specific to the antigen, said inert organic compound is an inert protein and said aqueous media are solutions.

57. A method for forming multimolecular immunologically complexed films comprising the steps of treating a metallized substrate with a monomolecular layer of an immunologically reactive antigen by forming a dilute first solution of said antigen, immersing the substrate in said first solution sufficiently to coat the substrate with a partial monomolecular layer of the antigen, and removing the partially coated substrate from the first solution, and immersing the partially coated substrate in a serum solution comprising an immunologically reactive antibody and inert organic compound whereby inert organic compound adheres to the substrate to complete a monomolecular layer of antigen molecules separated from each other by inert organic compound molecules, and the antibody molecules in the serum forms a second layer.

58. A method as defined in claim 57 wherein said metallized substrate is slide shaped, said immunological reaction is between a protein antigen and a protein antibody specific to said antigen and said inert organic compound is an inert protein.

* * * * *